United States Patent [19]

Nieuwoudt

[11] Patent Number: Plant 6,047

[45] Date of Patent: Dec. 1, 1987

[54] VARIETY OF NAVEL ORANGE TREE

[76] Inventor: Hermias C. Nieuwoudt, The Farm Korhaanshoogte, Citrusdal, Cape Province, South Africa

[21] Appl. No.: 484,597

[22] Filed: Apr. 13, 1983

[30] Foreign Application Priority Data

Apr. 13, 1982 [ZA] South Africa ..... PT 263

[51] Int. Cl.[4] ..... A01H 5/03

[52] U.S. Cl. ..... Plt./45

[58] Field of Search ..... Plt. 45

[56] References Cited

U.S. PATENT DOCUMENTS

P.P. 2,970 6/1970 Walker et al. ..... Plt. 45

*Primary Examiner*—Robert E. Bagwill

*Attorney, Agent, or Firm*—Ladas & Parry

[57] ABSTRACT

A late ripening navel orange bearing fruit with a thin peel which is not prone to splitting.

2 Drawing Figures

This invention is directed to a novel variety of navel orange tree, characterized in that it has a very firm citrus fruit which ripens 2-3 months later than Washington Navel oranges and a thin peel which is not prone to splitting. More particularly, the invention is directed to a novel variety of the genus citrus, species *chinensis*, and family rutaceae, which was discovered on a plantation in the Citrusdal district, Cape Province, South Africa.

Other distinctive characteristics of the new variety are exemplified in the accompanying illustrations.

Figure 1:
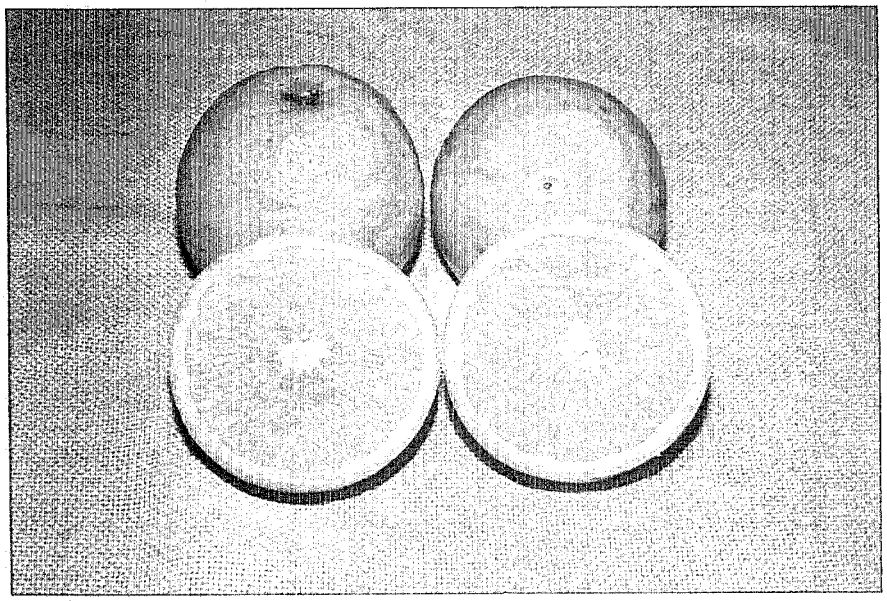
Figure 2:
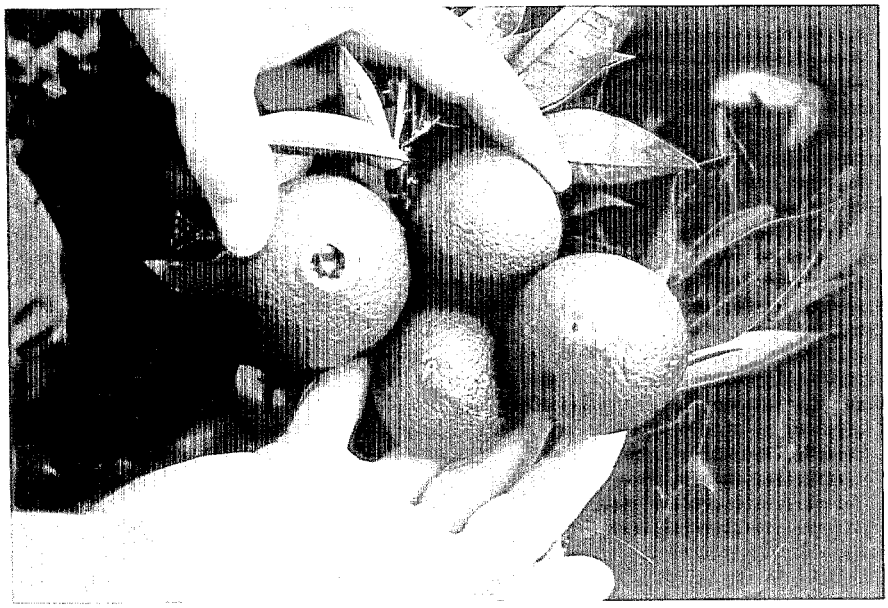

FIG. 1 shows two whole fruit of the new variety, from the top and bottom respectively, illustrating the exterior of the fruit, as well as transverse mid-sections of the fruit in a plane substantially perpendicular to the axis of the fruit, illustrating the interior of the fruit; and FIG. 2 shows three whole fruit of the new variety, illustrating the distal end of the fruit in comparison with the distal end of a conventional navel orange shown on the extreme left, as well as portions of the stems and leaves of the new variety.

In 1962, 2000 Washington navel orange trees were planted on a farm in the Citrusdal district about 80 miles from the Atlantic Ocean. This is a winter rainfall region, with an average precipitation of approximately 20 inches per year. The average maximum summer temperature is about 36° C. The soil has a loamy, sandy texture.

Several years thereafter, one tree was discovered which differed from the rest. The tree grew more rapidly than the others from the original planting. In addition, the fruit was observed to be greener and less developed than that of the other trees, indicating that the tree was a novel variety of late navel. From this tree, 30 others were grafted by means of the Israeli method. A T-shaped cut was made in the bark of the tree and the bud from the novel variety grafted on at this cut. These trees are consistently producing late navels.

The novel variety of citrus trees, given the denomination Nieuwoudt, yields a flavorful and juicy fruit of excellent quality for consumption. The fruit has a slightly lighter than normal color. The time of maturity of the fruit in South Africa is between July and September. Tree ripening of the fruit takes place between August and November; fruit picked during October can be preserved at sub-ambient temperatures until February. Another notable characteristic of the fruit is that the inside remains very solid, thus providing a desirable firm, seedless citrus fruit.

A large variation in fruit size is observed. In addition, there is some variation in shape from slightly pear-shaped to basically round. The distal end of the fruit is very slightly nippled. In order to insure that no undesirable fruit shape is propagated, appropriate selection must be effected. Some thorns are present on juvenile trees but no on mature trees. In other respects, the tree and fruit are identical to those of known navels, in particular, Washington navels.

The results of a quality test conducted on representative fruit from the novel variety are as follows:

The mass (of 20 oranges)—4310 grams
The mass of peels plus pulp—2120 grams
Percentage juice—50.8
Fiber strength (average for 20 oranges)—3.9
Thickness of peel (average for 20 oranges)—5.1 mm
Total dissolved solids (TDS)—14.7%
Acid content—0.63%
TDS/acid ratio—23.3
No seeds.

I claim:

1. A novel variety of navel orange tree substantially as shown and described, characterized by a firm, late-ripening fruit of slightly lighter than normal color with a thin peel which is not prone to splitting.

* * * * *

UNITED STATES PATENT AND TRADEMARK OFFICE

CERTIFICATE OF CORRECTION

PATENT NO. : PLANT 6,047

DATED : December 1, 1987

INVENTOR(S) : Hermias Nieuwoudt

It is certified that error appears in the above-identified patent and that said Letters Patent is hereby corrected as shown below:

Page 1, Column 2, line 20, should read

--trees but not on mature trees. In other respects, the tree --

Signed and Sealed this

Sixteenth Day of August, 1988

*Attest:*

DONALD J. QUIGG

*Attesting Officer*

*Commissioner of Patents and Trademarks*